United States Patent [19]

Pitteloud et al.

[11] Patent Number: 5,401,845
[45] Date of Patent: Mar. 28, 1995

[54] ASYMMETRIC ARYL PHOSPHITES

[75] Inventors: Rita Pitteloud, Praroman; Peter Hofmann, Basel, both of Switzerland; Rudolf Maul, Lorsch/Hessen; Volker Schenk, Bensheim, both of Germany; Eduard Troxler, Basel, Switzerland; Horst Zinke, Reichelsheim/Odw., Germany

[73] Assignee: Ciba-Geigy Corporation, Ardsley, N.Y.

[21] Appl. No.: 212,756

[22] Filed: Mar. 11, 1994

Related U.S. Application Data

[60] Division of Ser. No. 49,647, Apr. 20, 1993, Pat. No. 5,322,871, which is a continuation of Ser. No. 857,523, Mar. 25, 1992, abandoned.

[30] Foreign Application Priority Data

Mar. 26, 1991 [CH] Switzerland .......................... 913/91

[51] Int. Cl.$^6$ .................. C07F 9/146; C07F 9/145
[52] U.S. Cl. .................................. 546/25; 558/92; 558/95; 558/156; 558/158; 558/160; 558/167; 558/170; 558/180; 558/192; 558/202; 558/218
[58] Field of Search ............ 558/218, 156, 202, 92, 558/95, 158, 160, 167, 170, 180, 192, 202, 218; 546/21, 22, 25

[56] References Cited

U.S. PATENT DOCUMENTS

| | | | |
|---|---|---|---|
| 2,866,807 | 12/1958 | Boyer et al. | 524/151 |
| 2,877,259 | 3/1959 | Bill | 558/218 |
| 3,281,506 | 10/1966 | Shepard et al. | |
| 3,558,554 | 1/1971 | Kuriyama et al. | |
| 4,079,103 | 3/1978 | Mazour | |
| 4,233,208 | 11/1980 | Spivack | |
| 4,276,233 | 6/1981 | Markezich et al. | 558/218 |
| 4,348,308 | 9/1982 | Minagawa et al. | |
| 4,356,129 | 10/1982 | Hucks et al. | |
| 4,444,929 | 4/1984 | Chaser | |
| 4,584,146 | 4/1986 | Chasar | |
| 4,707,509 | 11/1987 | Fisch et al. | 524/151 |
| 4,739,000 | 4/1988 | Burton | 558/156 |
| 4,814,367 | 3/1989 | Loiotile et al. | |
| 5,021,481 | 6/1991 | Galbo et al. | 546/22 |
| 5,254,709 | 10/1993 | Hunter | 558/218 |

FOREIGN PATENT DOCUMENTS

| | | |
|---|---|---|
| 4306747 | 9/1993 | Germany. |
| 54-41948 | 4/1979 | Japan. |
| 325437 | 2/1991 | Japan. |

OTHER PUBLICATIONS

Chem. Abst. 91, 58158c (1979).
Chem. Abstr. 91, 581646 (1979).
Derwent Abst. 44760B/24.
Derwent Abst. 87-147658/21.
Derwent Abst. 13945C/08.
Derwent Abst. 10380C/06.
Derwent Abst. 34457B/18.
Chem. Abst. 92, 216251e (1980).
H. G. Cook, et al., J. Chem. Soc. 1949, Part IV, 2921.
Chem. Absts. 60, 1571g (1964).
J. Michalski, et al., J. Chem. Soc. 1961, 4904.
Derwent Abst. 91-077904/11.
Chem. Absts. 91:92485s (1979).
Chem. Absts. 91:58133r (1979).

Primary Examiner—Veronica P. Hoke
Attorney, Agent, or Firm—Luther A. R. Hall

[57] ABSTRACT

Compounds of the formula I

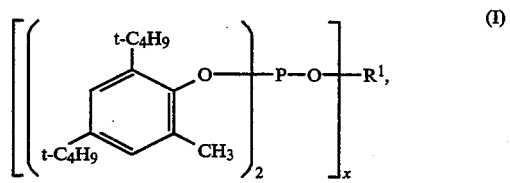

in which x is 1, 2 or 3, and, if x=1, $R^1$ is $C_1$–$C_{30}$alkyl, $C_1$–$C_{18}$alkyl substituted by halogen, —$COOR^2$, —CN, —$NR^3R^4$ or by —$CONR^3R^4$, $C_2$–$C_{18}$alkyl which is interrupted by —$NR^5$—, —O— or —S—, $C_3$–$C_{18}$alkenyl, $C_5$–$C_{12}$cycloalkyl, phenyl-$C_1$–$C_4$alkyl, phenyl which is unsubstituted or substituted by $C_1$–$C_{12}$alkyl, halogen, phenyl- (Abstract continued on next page.)

Abstract—continued $C_1$-$C_4$alkyl and/or $C_1$-$C_4$alkoxy, or $R_1$ is naphthyl, a radical of the formula

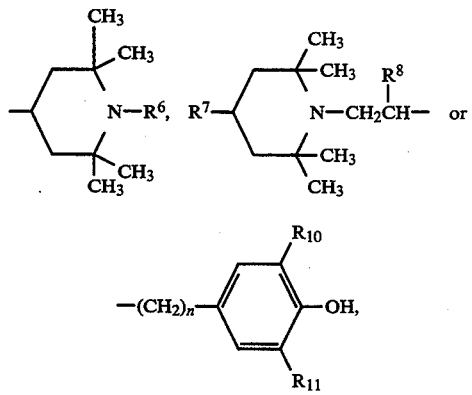

$R_2$, $R_3$, $R_4$ and $R_5$, independently of one another, are hydrogen, $C_1$-$C_{18}$alkyl, $C_5$-$C_{12}$cycloalkyl or phenyl-$C_1$-$C_4$alkyl, $R_6$ is hydrogen, methyl, allyl or benzyl, $R_7$ is hydrogen or —$OR_9$, $R_8$ is hydrogen or methyl, $R_9$ is hydrogen or $C_1$-$C_{30}$alkyl, $R_{10}$ and $R_{11}$, independently of one another, are hydrogen or $C_1$-$C_8$alkyl, and n is 3-6, with the proviso that $R_1$ is not a phenyl radical which is substituted in both ortho-positions to the carbon atom bonded to the oxygen atom, if x=2, $R_1$ is $C_2$-$C_{18}$alkylene, $C_2$-$C_{18}$alkylene which is interrupted by —$NR_5$, —O— or —S—, or is a

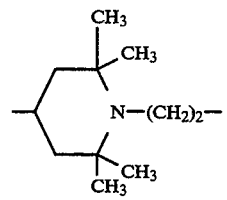

radical, and, if x=3, $R_1$ is $C_4$-$C_{12}$alkanetriyl or a

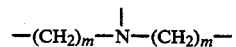

group in which m is 1-4, are suitable as stabilizers for organic materials which are sensitive to thermal, oxidative and/or photoinduced degradation.

9 Claims, No Drawings

ASYMMETRIC ARYL PHOSPHITES

This is a divisional of Ser. No. 08/049,647, filed Apr. 20, 1993, now U.S. Pat. No. 5,322,871, which is a continuation of Ser. No. 07/857,523, filed Mar. 25, 1992, now abandoned.

The invention relates to novel phosphites, to the use thereof as stabilisers, to a novel phosphorochloridite as intermediate, and to compositions containing said phosphites.

A number of patent applications, eg. JP-A-54/039 455, JP-A-54/036 363, JP-A-54/055 043 and JP-A-62/086 036, disclose principally symmetrically substituted triaryl phosphites as stabilisers, and JP-A-54/041 948 uses these phosphites together with other stabilisers in synthetic resin compositions. One of the concrete examples given here is tris(2,4-di-tert-butyl-6-methylphenyl)phosphite. Phosphites containing at least one aryl radical are disclosed in JP-A-55/005 927, JP-A-54/163 938, U.S. Pat. No. 4,348,308 and U.S. Pat. No. 3,558,554. The aryl radical in U.S. Pat. No. 3,558,554 is preferably tert-butyl-substituted p-cresyl. U.S. Pat. No. 4,348,308 discloses, for example, compounds such as bis(2,4-di-tert-butylphenyl)cyclohexyl phosphite and bis(2-tert-butylphenyl)isodecyl phosphite. U.S. Pat. No. 4,444,929 uses compounds such as bis(2-tert-butyl-4-methylphenyl) 2,6-di-tert-butyl-4-methylphenyl phosphite in stabiliser mixtures. Analogues of the intermediate for the preparation of the compounds according to the invention have already been disclosed in the literature. Thus, U.S. Pat. No. 4,584,146 and U.S. Pat. No. 4,444,929 disclose bis(2,6-di-tert-butyl-4-methylphenyl)-phosphorochloridite as an intermediate in the preparation of phosphites. U.S. Pat. No. 4,233,208 uses bis(2,6-di-tert-butyl-4-methylphenyl) phosphorochloridite and similar chlorides and hydroxides as stabilisers.

There continues to be a demand for effective stabilizers for organic materials which are sensitive to photoinduced and/or thermooxidative degradation.

The invention relates to compounds of the formula I

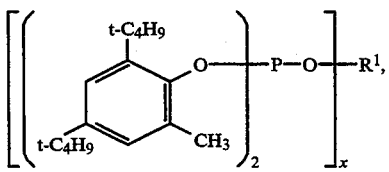

in which x is 1, 2 or 3, and, if x=1, $R^1$ is $C_{14}$ $C_{30}$alkyl, $C_1$–$C_{18}$alkyl substituted by halogen, —COOR$^2$, —CN, —NR$^3$R$^4$ or by —CONR$^3$R$^4$, $C_2$–$C_{18}$alkyl which is interrupted by —NR$^5$—, —O— or —S—, $C_3$–$C_{18}$alkenyl, $C_5$–$C_{12}$cycloalkyl, phenyl-$C_1$–$C_4$alkyl, phenyl which is unsubstituted or substituted by $C_1$–$C_{12}$alkyl, halogen, phenyl-$C_1$–$C_4$alkyl and/or $C_1$–$C_4$alkoxy, or $R_1$ is naphthyl, a radical of the formula

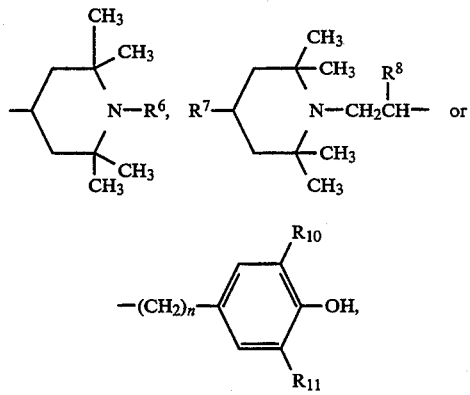

$R_2$, $R_3$, $R_4$ and $R_5$, independently of one another, are hydrogen, $C_1$–$C_{18}$alkyl, $C_5$–$C_{12}$cycloalkyl or phenyl-$C_1$–$C_4$alkyl, $R^6$ is hydrogen, methyl, allyl or benzyl, $R^7$ is hydrogen or —OR$^9$, $R^8$ is hydrogen or methyl, $R^9$ is hydrogen or $C_1$–$C_{30}$alkyl, $R^{10}$ and $R^{11}$, independently of one another, are hydrogen or $C_1$–$C_8$alkyl, and n is 3–6, with the proviso that $R^1$ is not a phenyl radical which is substituted in both ortho-positions to the carbon atom bonded to the oxygen atom, if x=2, $R^1$ is $C_2$–$C_{18}$alkylene, $C_2$–$C_{18}$alkylene which is interrupted by —NR$^5$—, —O— or —S—, or is a

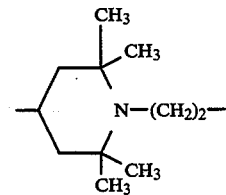

radical, and, if x=3, $R^1$ is $C_4$–$C_{12}$alkanetriyl or a

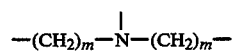

group in which m is 1–4.

$C_1$–$C_{30}$alkyl $R^1$ may be linear or branched and is, for example, methyl, ethyl, isomers of propyl, butyl, pentyl, hexyl, heptyl, octyl, nonyl, decyl, dodecyl, tetradecyl, heptadecyl, octadecyl, icosyl, tetracosyl or triacontyl. Alkyl $R^1$ is in particular $C_1$–$C_{24}$alkyl, very particularly $C_1$–$C_{18}$alkyl, preferably $C_1$–$C_{12}$alkyl, eg. $C_1$–$C_4$alkyl.

$C_1$–$C_{18}$alkyl $R^2$, $R^3$, $R^4$ and $R^5$ may be linear or branched and are defined, for example, as for $C_1$–$C_{30}$alkyl $R^1$ apart from the corresponding number of carbon atoms. Preference is given to $C_1$–$C_{12}$alkyl, in particular $C_1$–$C_4$alkyl.

Halogen-substituted $C_1$–$C_{18}$alkyl $R^1$ may be linear or branched and monosubstituted or polysubstituted, eg. monosubstituted to trisubstituted, in particular monosubstituted or disubstituted, and is, for example, chloromethyl, dichloromethyl, trichloromethyl, chloroethyl, dichloroethyl, chloropropyl, fluoromethyl, trifluoromethyl, trifluoroethyl, trifluoropropyl, etc.

—COOR$^2$-substituted $C_1$–$C_{18}$alkyl $R^1$ is, for example, methyl, ethyl, propyl, butyl, pentyl, hexyl, heptyl, octyl, nonyl, decyl, dodecyl or octadecyl, each of which is substituted by methoxycarbonyl, ethoxycarbonyl, isomers of propoxycarbonyl, butoxycarbonyl, pentoxycarbonyl, hexyloxycarbonyl, heptyloxycarbonyl, ethylhexyloxycarbonyl, decyloxycarbonyl, dodecyloxycarbonyl, cyclohexyloxycarbonyl, or tolyloxycarbonyl, in particular by methoxycarbonyl or ethoxycarbonyl, and is preferably methyl or ethyl, in particular methyl, each of which is substituted by methoxycarbonyl, ethoxycarbonyl or in particular butoxycarbonyl.

—CONR$^3$R$^4$-substituted C$_1$–C$_{18}$alkyl R$^1$ is, for example, methyl, ethyl, propyl, butyl, pentyl, hexyl, heptyl, octyl, nonyl, decyl, dodecyl or octadecyl, each of which is substituted by dimethylaminocarbonyl, diethylaminocarbonyl, dibutylaminocarbonyl or ethylmethylaminocarbonyl, in particular dimethyl- or diethylaminocarbonyl, and is preferably methyl, ethyl or propyl, each of which is substituted by dimethylaminocarbonyl or diethylaminocarbonyl, in particular propyl which is substituted by dimethylaminocarbonyl.

CN-substituted C$_1$–C$_{18}$alkyl R$^1$ is, for example, cyanomethyl, cyanoethyl, cyanopropyl, cyanobutyl, cyanopentyl, cyanohexyl, cyanooctyl, cyanodecyl, cyanododecyl or cyanooctadecyl, in particular cyanoethyl.

C$_2$–C$_{18}$Alkyl R$^1$ which is interrupted by —O—, —S— or —NR$^5$— units contain, for example, the structural units —CH$_2$—CH$_2$—O—, —CH$_2$—CH$_2$—S— or —CH$_2$—CH$_2$—NR$^5$—. The —NR$^5$—, —O— or —S— groups can occur once or more than once in the chain. Other examples of C$_2$–C$_{18}$alkyl R$^1$ which is interrupted by —O—, —S— or —NR$^5$— units are methyl, ethyl, propyl, butyl, pentyl, hexyl, heptyl, octyl, nonyl, decyl, dodecyl or octadecyl, each of which is substituted by methoxy, ethoxy, propoxy, butoxy, methylthio, ethylthio, propylthio, butylthio, dimethylamino, diethylamino, dipropylamino, etc, in particular methoxy or ethoxy, preferably ethyl which is substituted by methoxy.

C$_5$–C$_{12}$Cycloalkyl R$^1$, R$^2$, R$^3$, R$^4$ and R$^5$ may be, for example, cyclopentyl, cyclohexyl, cycloheptyl, cyclooctyl, cyclodecyl or cyclododecyl, preferably cyclopentyl or cyclohexyl, in particular cyclohexyl.

Phenyl-C$_1$–C$_4$alkyl R$^1$, R$^2$, R$^3$, R$^4$ and R$^5$ are, for example, benzyl, 1-phenylethyl, 2-phenylethyl, 3-phenylpropyl, α-methylbenzyl, α,α-dimethylbenzyl, etc, preferably benzyl or 1-phenylethyl.

An aromatic radical R$^1$ is preferably phenyl.

Substituted phenyl R$^1$ preferably contains 1 to 3 substituents, in particular 1 or 2 substituents, and is, for example, chlorophenyl, dichlorophenyl, trichlorophenyl, fluorophenyl, difluorophenyl, tolyl, dimethylphenyl, mesityl, ethylphenyl, diethylphenyl, isopropylphenyl, tert-butylphenyl, benzylphenyl, phenylethylphenyl, di-t-butylphenyl, methyl-di-tert-butylphenyl, dodecylphenyl, methoxyphenyl, dimethoxyphenyl, ethoxyphenyl, hexyloxyphenyl, methoxyethylphenyl or ethoxymethylphenyl, in particular p-tert-butylphenyl. Alkyl and alkoxy as aryl substituents preferably have 1–4 carbon atoms and are, in particular, methyl, tert-butyl or methoxy, preferably tert-butyl.

An aromatic radical R$^1$ is in particular phenyl which is unsubstituted or substituted by an alkyl group.

Halogen is, in particular, chlorine, bromine or fluorine.

Of particular interest are compounds of the formula I in which, if x=1, R$^1$ is C$_1$–C$_{30}$alkyl, C$_1$–C$_{18}$alkyl substituted by halogen, —COOR$^2$, —CN, —NR$^3$R$^4$ or by —CONR$^3$R$^4$, C$_2$–C$_{18}$alkyl which is interrupted by —NR$^5$—, —O— or —S—, C$_3$–C$_{18}$alkenyl, C$_5$–C$_{12}$cycloalkyl, phenyl-C$_1$–C$_4$alkyl, phenyl which is unsubstituted or substituted by C$_1$–C$_{12}$alkyl, halogen, phenyl-C$_1$–C$_4$alkyl and/or C$_1$–C$_4$alkoxy, or R$_1$ is naphthyl, a radical of the formula

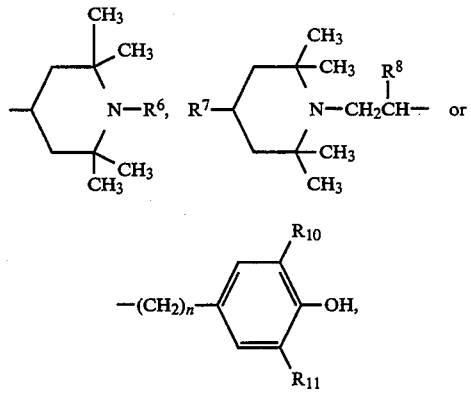

if x=2, R$^1$ is C$_2$–C$_{18}$alkylene, C$_2$–C$_{18}$alkylene which is interrupted by —NR$^5$—, —O— or —S—, or is a

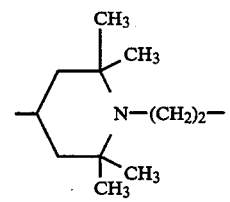

radical, and,
if x=3, R$^1$ is C$_4$–C$_{12}$alkanetriyl or a

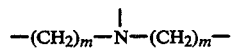

group in which m is 1–4.

Other particularly interesting compounds of the formula I are those in which, if x=1, R$^1$ is C$_1$–C$_{24}$alkyl, C$_1$–C$_{12}$alkyl substituted by halogen; —COOR$^2$, —CN, —NR$^3$R$^4$ or by —CONR$^3$R$^4$, C$_2$–C$_{18}$alkyl which is interrupted by —NR$^5$—, —O— or —S—, C$_3$–C$_{18}$alkenyl, C$_5$–C$_{12}$cycloalkyl, phenyl-C$_1$–C$_4$alkyl, phenyl which is unsubstituted or substituted by C$_1$–C$_{12}$alkyl, halogen, phenyl-C$_1$–C$_4$alkyl and/or C$_1$–C$_4$alkoxy, or R$_1$ is naphthyl, a radical of the formula

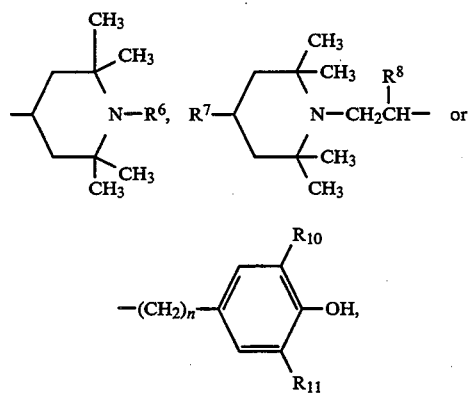

if x=2, $R^1$ is $C_2$-$C_{12}$alkylene, $C_2$-$C_{12}$alkylene which is interrupted by —$NR^5$—, —O— or —S—, or is a

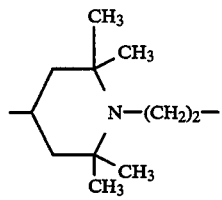

radical, and $R^{10}$ and $R^{11}$, independently of one another, are hydrogen or $C_1$-$C_4$alkyl, and,
if x=3, $R^1$ is $C_4$-$C_{12}$alkanetriyl or a

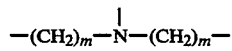

group in which m is 1-4.

Preference is given to compounds of the formula I in which, if x=1, $R^1$ is $C_1$-$C_{20}$alkyl, $C_1$-$C_8$alkyl which is substituted by halogen, —$COOR^2$, —CN or —$NR^3R^4$, $C_2$-$C_8$alkyl which is interrupted by —O— or —S—, $C_3$-$C_8$alkenyl, $C_5$-$C_8$cycloalkyl, phenyl which is unsubstituted or substituted by $C_1$-$C_{12}$alkyl or phenyl-$C_1$-$C_4$alkyl, or $R_1$ is naphthyl, a radical of the formula

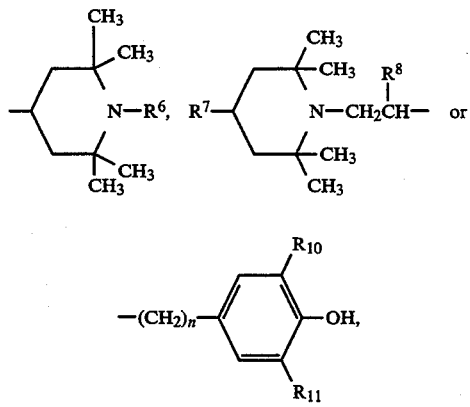

$R^6$ is hydrogen or methyl, and $R^8$ and $R^9$ are hydrogen, if x=2, $R^1$ is $C_2$-$C_8$alkylene or $C_2$-$C_8$alkylene which is interrupted by —$NR^5$— or —O—, and, if x=3, $R^1$ is a

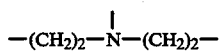

radical.

Further interesting compounds of the formula I are those in which, if x=1, $R^1$ is $C_1$-$C_{18}$alkyl which is unsubstituted or substituted by halogen, —$COOR^2$, —CN or —$NR^3R^4$, $C_2$-$C_{18}$alkyl which is interrupted by —$NR^5$—, —O— or —S—, $C_3$-$C_6$alkenyl, $C_5$-$C_8$cycloalkyl, phenyl-$C_1$-$C_4$alkyl, a radical of the formula

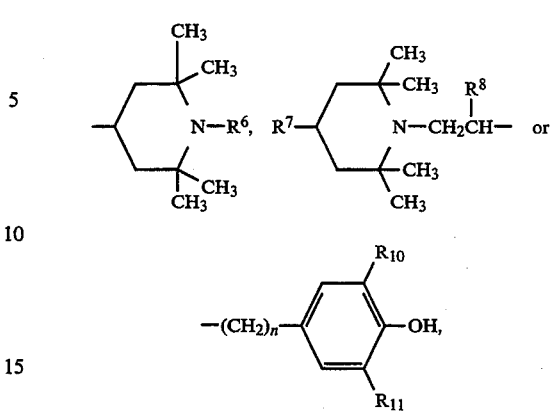

and,
if x=2, $R^1$ is $C_2$-$C_{12}$alkylene, $C_2$-$C_{12}$alkylene which is interrupted by —$NR^5$—, —O— or —S—, or is a

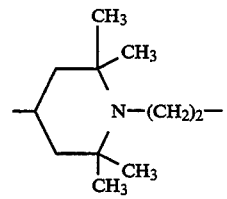

radical, and,
if x=3, $R^1$ is $C_4$-$C_{12}$alkanetriyl or a

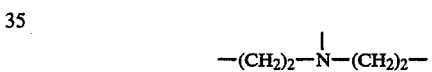

group.

Preference is given to compounds of the formula I in which x=1, $R^1$ is $C_1$-$C_{12}$alkyl which is unsubstituted or substituted by halogen, —$COOR^2$, —CN or —$NR^3R^4$, $C_2$-$C_{12}$alkyl which is interrupted by —$NR^5$—, —O— or —S—, or is phenyl-$C_1$-$C_4$alkyl or $C_5$-$C_7$cycloalkyl.

Preference is furthermore given to compounds of the formula I in which $R^1$ is $C_1$-$C_4$alkyl.

Particular emphasis should also be attached to compounds of the formula I in which $R^1$ is as defined above, but is not unsubstituted or $C_1$-$C_{12}$alkyl-, halogen- or $C_1$-$C_4$alkoxy-substituted phenyl or naphthyl.

Also worthy of mention in particular are compounds of the formula I in which $R^1$ is $C_1$-$C_{18}$alkyl, $C_5$-$C_7$cycloalkyl or phenyl-$C_1$-$C_4$alkyl, in particular $C_1$-$C_{18}$alkyl.

The compounds of the formula I can be obtained by processes which are known per se in chemistry. DE-A-2 950 694 describes a process for the preparation of corresponding compounds by reacting a phosphorus trihalide, a phosphorous acid monoester dihalide or a phosphorous acid diester halide with a phenol in the presence of an alkali metal hydroxide or alkaline earth metal hydroxide.

The compounds according to the invention can accordingly be prepared by substituting the chlorine in the diaryl phosphorochloridite by an alcohol or a phenol in the presence of a base.

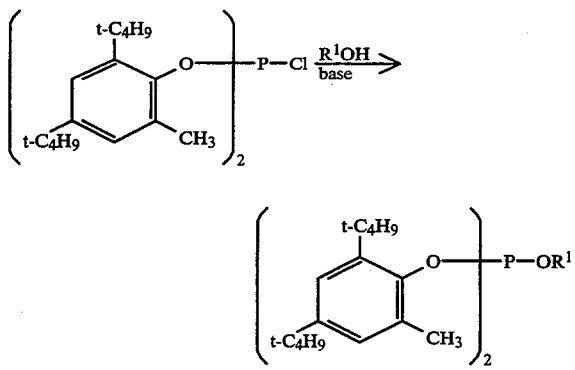

$R^1$ is as defined above.

In order to prepare dimeric and trimeric compounds of the formula I, the corresponding polyols are used.

The bases used can be organic bases or inorganic bases. Examples of organic bases are tertiary amines, eg. trimethylamine, triethylamine, N,N-dimethylaniline, N,N-diethylaniline or pyridine. Examples of inorganic bases are alkali metal hydroxides, for example sodium hydroxide or potassium hydroxide, or alkali metal carbonates, for example sodium carbonate or potassium carbonate.

The substitution reaction temperatures are, for example, from −30° C. to +150° C., preferably from −10° C. to +70° C.

Solvents which can be employed are aliphatic and aromatic, simple or halogenated hydrocarbons or ethers. Examples of suitable aromatic hydrocarbons are benzene, toluene and xylene, and an example of a suitable chlorinated aromatic hydrocarbon is chlorobenzene. Examples of aliphatic hydrocarbons which can be used as solvents are hexane, pentane and further petroleum ether fractions. Examples of suitable halogenated aliphatic hydrocarbons are methylene chloride and chloroform. Examples of suitable ethers are diethyl ether, dibutyl ether and tetrahydrofuran.

The diaryl phosphorochloridite (II) and the alcohol $R^1OH$ are expediently employed in equivalent amounts. It is, however, also possible, for example, to use an excess of alcohol, for example 1.05–1.2 equivalents.

A further method of preparing compounds according to the invention is to condense 2 equivalents of 2,4-di-tert-butyl-6-methylphenol with one equivalent of a phosphorus compound $R^1O$—$PCl_2$ in the presence of an organic base.

The invention also relates to the compound of the formula II

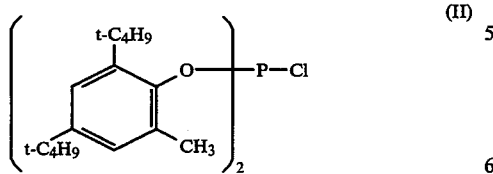

(II)

and to the use thereof for the preparation of compounds of the formula I.

The preparation of phosphorochloridites is known to persons skilled in the art and is described in numerous publications. The novel phosphorochloridite of the formula II can be prepared by analogous processes. For instance, H. G. Cook et al., J. Chem. Soc. 1949, IV, 2921–2927, and A. J. Razumov et at., Chemical Abstracts 60, 1571g (1964), describe the preparation of corresponding chlorides by reacting phosphorus trichloride with alkanols in the presence of N,N-dimethylaniline or N,N-diethylaniline as acid acceptor. J. Michalski et at., J. Chem. Soc. 1961, 4904, disclose a variant of this process in which the acid acceptor employed is a pyridine/diethylaniline mixture. Reactions of phosphorus trichloride with hindered phenols are disclosed in U.S. Pat. No. 3,281,506 and U.S. Pat. No. 4,584,146. H. G. Cook et al., J. Chem. Soc., 1949, IV, 2921–2927 indicate a further method of preparing phosphorochloridites analogous to the formula II. They react phosphorus trichloride with symmetrical trialkyl phosphites. A variant of this process is described in U.S. Pat. No. 4,079,103.

Bis(2,4-di-tert-butyl-6-methyl) phosphorochloridite can also be prepared directly in the melt without solvents. This allows the preparation of the phosphites of the formula I without isolation of the intermediate.

The compounds of the formula I are highly suitable for stabilising organic materials against photoinduced, thermal and/or oxidative degradation. The invention therefore also relates to compositions comprising an organic material which is sensitive to degradation reactions of this type, and at least one compound of the formula I, and to the use of compounds of the formula I as stabilisers for organic materials against said types of degradation.

Examples of such materials are:

1. Polymers of monoolefins and diolefins, for example polypropylene, polyisobutylene, polybut-1-ene, polymethylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE).

2. Mixtures of the polymers mentioned under 1), for example mixes of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene-propylene copolymers, linear low density polyethylene (LLDPE) and its mixtures with low density polyethylene (LDPE), propylene-but-1-ene, propylene-isobutylene, ethylene-but-1-ene, ethylene-hexene, ethylene-methylpentene, ethylene-heptene, ethylene-octene, propylene-butadiene, isobutylene-isoprene, ethylene-alkyl acrylate, ethylene-alkyl methacrylate, ethylene-vinyl acetate or ethylene-acrylic acid copolymers and their salts (ionomers) and terpolymers of ethylene with propylene and a diene, such as hexadiene, dicyclopentadiene or ethylidenenorbornene; as well as mixtures of such copolymers and their mixtures with polymers mentioned in 1), for example polypropylene/ethylene-propylene copolymers, LDPE/ethylene-vinyl acetate copolymers, LDPE/ethylene-acrylic acid copolymers, LLDPE/ethylene-vinyl acetate copolymers and LLDPE/ethylene-acrylic acid copolymers.

3a. Hydrocarbon resins (for example $C_5$–$C_9$) and hydrogenated modifications thereof (for example tackifiers).

4. Polystyrene, poly(p-methylstyrene), poly($\alpha$-methylstyrene).

5. Copolymers of styrene or $\alpha$-methylstyrene with dienes or acrylic derivatives, for example styrene-butadiene, styrene-acrylonitrile, styrene-alkyl methacrylate, styrene-butadiene-alkyl acrylate, styrene-maleic anhydride, styrene-acrylonitrile-methyl acrylate; high impact strength mixtures of styrene copolymers and another polymer, for example a polyacrylate, a diene polymer or an ethylene-propylene-diene terpolymer, and block copolymers of styrene, for example styrene-butadiene-styrene, styrene-isoprenestyrene, styrene-ethylene/butylene-styrene or styrene-ethylene/-propylene-styrene.

6. Graft copolymers of styrene or $\alpha$-methylstyrene, for example styrene on polybutadiene, styrene on polybutadiene-styrene or polybutadiene-acrylonitrile; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or methacrylates on polybutadiene, styrene and acrylonitrile on ethylene-propylene-diene terpolymers, styrene and acrylonitrile on polyalkyl acrylates or polyalkyl methacrylates, styrene and acrylonitrile on acrylate-butadiene copolymers, as well as mixtures thereof with the copolymers mentioned under 5), for instance the copolymer mixtures known as ABS, MBS, ASA or AES polymers.

7. Halogen-containing polymers, such as polychloroprene, chlorinated rubber, chlorinated or chlorosulfonated polyethylene, copolymers of ethylene and chlorinated ethylene, epichlorohydrin homo- and copolymers, in particular polymers from halogen-containing vinyl compounds, for example polyvinyl chloride, polyvinylidene chloride, polyvinyl fluoride, polyvinylidene fluoride, as well as copolymers thereof, for example vinyl chloride-vinylidene chloride, vinyl chloride-vinyl acetate or vinylidene chloride-vinyl acetate copolymers.

8. Polymers derived from $\alpha,\beta$-unsaturated acids and derivatives thereof, such as polyacrylates and polymethacrylates, polyacrylamides and polyacrylonitriles.

9. Copolymers from the monomers mentioned under 8) with each other or with other unsaturated monomers, for instance acrylonitrile-butadiene, acrylonitrile-alkyl acrylate, acrylonitrile-alkoxyalkyl acrylate or acrylonitrile-vinyl halide copolymers or acrylonitrile-alkyl methacrylate-butadiene terpolymers.

10. Polymers derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; and their copolymers with olefins mentioned in 1) above.

11. Homopolymers and copolymers of cyclic ethers, such as polyalkylene glycols, polyethylene oxide, polypropylene oxide or copolymers thereof with bisglycidyl ethers.

12. Polyacetals, such as polyoxymethylene and those polyoxymethylenes which contain comonomers, for example ethylene oxide; polyacetals modified with thermoplastic polyurethanes, acrylates or MBS.

13. Polyphenylene oxides and sulfides, and mixtures thereof with styrene polymers or polyamides.

14. Polyurethanes derived from polyethers, polyesters or polybutadienes with terminal hydroxyl groups on the one hand and aliphatic or aromatic polyisocyanates on the other, and precursors thereof.

15. Polyamides and copolyamides which are derived from diamines and dicarboxylic acids and/or from aminocarboxylic acids or the corresponding lactams, such as nylon 4, nylon 6, nylon 6/6, 6/10, 6/9, 6/12 and 4/6, nylon 11, nylon 12, aromatic polyamides obtained from m-xylene, diamine and adipic acid; polyamides prepared from hexamethylenediamine and isophthalic and/or terephthalic acid and optionally an elastomer as modifier, for example poly-2,4,4-trimethylhexamethylene terephthalamide or poly-m-phenylene isophthalamide. Block copolymers of the aforementioned polyamides with polyolefins, olefin copolymers, ionomers or chemically bonded or grafted elastomers; or with polyethers, for instance with polyethylene glycol, polypropylene glycol or polytetramethylene glycol. Further, EPDM- or ABS-modified polyamides or copolyamides; and polyamides condensed during processing ("RIM polyamide systems").

16. Polyureas, polyimides, polyamide-imides and polybenzimidazoles.

17. Polyesters derived from dicarboxylic acids and diols and/or from hydroxycarboxylic acids or the corresponding lactones, such as polyethylene terephthalate, polybutylene terephthalate, poly-1,4-dimethylolcyclohexane terephthalate and polyhydroxybenzoates as well as block polyether-esters derived from polyethers having hydroxyl end groups; also polycarbonate- or MBS-modified polyesters.

18. Polycarbonates and polyester carbonates.

19. Polysulfones, polyether sulfones and polyether ketones.

20. Crosslinked polymers derived from aldehydes on the one hand and phenols, urea or melamine on the other, such as phenol/formaldehyde resins, urea/-formaldehyde resins and melamine/formaldehyde resins.

21. Drying and non-drying alkyd resins.

22. Unsaturated polyester resins derived from copolyesters of saturated and unsaturated dicarboxylic acids with polyhydric alcohols, and vinyl compounds as crosslinking agents, and also halogen-containing modifications thereof of low inflammability.

23. Crosslinkable acrylic resins, derived from substituted acrylic esters, for example epoxy acrylates, urethane acrylates or polyester acrylates.

24. Alkyd resins, polyester resins or acrylate resins crosslinked with melamine resins, urea resins, polyisocyanates or epoxy resins.

25. Crosslinked epoxy resins derived from polyepoxides, for example from bisglycidyl ethers or from cycloaliphatic diepoxides.
26. Natural polymers, such as cellulose, natural rubber, gelatin and derivatives thereof which are chemically modified in a polymer-homologous manner, such as cellulose acetates, cellulose propionates and cellulose butyrates, or cellulose ethers, such as methylcellulose; and colophony resins and their derivatives.
27. Mixtures (polyblends) of polymers as mentioned above, for example PP/EPDM, polyamide-/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.
28. Naturally occuring and synthetic organic substances which are pure monomeric compounds or mixtures thereof, for example mineral oils, animal or vegetable fats, oils and waxes, or oils, waxes and fats based on synthetic esters (for example phthalates, adipates, phosphates or trimellitates), and blends of synthetic esters with mineral oils in any desired weight ratios, as used, for example, as spinning preparations, and aqueous emulsions thereof.
29. Aqueous emulsions of natural or synthetic rubbers, for example natural rubber latex or latexes of carboxylated styrene-butadiene copolymers.

The organic materials to be protected are preferably natural, semisynthetic or preferably synthetic organic materials. Particular preference is given to thermoplastic polymers, in particular PVC or polyolefins, for example polyethylene and polypropylene (PP).

The compositions according to the invention expediently contain the compounds of the formula I in amounts of from 0.01 to 10% by weight, for example from 0.05 to 5% by weight, preferably from 0.05 to 3% by weight, but in particular from 0.1 to 2% by weight. It is possible for the compositions to contain one or more compounds of the formula I, and the per cent by weight data relate to! the total amount of these compounds. The calculation is based on the total weight of the organic material without the compounds of the formula I. Incorporation into the materials can be effected, for example, by mixing in or applying the compounds of the formula I and, if desired, further additives by methods which are conventional in industry. If the materials are polymers, in particular synthetic polymers; incorporation can take place before or during moulding or by applying the dissolved or dispersed compounds to the polymer, if necessary with subsequent evaporation of the solvent. In the case of elastomers, these may also be stabilised as latexes. A further way of incorporating the compounds of the formula I into polymers is to add them before, during or immediately after the polymerization of the corresponding monomers or before the crosslinking. The compounds of the formula I can be added as such or in encapsulated form (for example in waxes, oils or polymers). If added before or during the polymerization, the compounds of the formula I can also act as regulators for the chain length of the polymers (chain terminators).

The compounds of the formula I or mixtures thereof can also be added to the plastics to be stabilised in the form of a masterbatch which contains these compounds, for example, in a concentration of from 2.5 to 25% by weight.

Incorporation of the compounds of the formula I can expediently be effected by the following methods:
- as an emulsion or dispersion (for example to latexes or emulsion polymers)
- as a dry mix during mixing of the additional components or polymer mixtures
- by direct addition into the processing apparatus (for example extruder, internal mixer, etc)
- as a solution or melt.

Polymer compositions according to the invention can be used in varous forms or convened into various products, for example as (into) films, fibres, tapes, moulding compositions, profiles or as binders for surface coatings, adhesives or adhesive cements.

As stated above, the organic materials to be protected are organic, preferably synthetic polymers. Particular preference is given to the protection of thermoplastic materials, in particular polyolefins. The excellent effectiveness of the compounds of the formula I as processing stabilisers (heat stabilisers) should be particularly emphasised. For this purpose, they are advantageously added to the polymer before or during processing thereof.

However, it is also possible to stabilise other polymers (for example elastomers) or lubricants or hydraulic fluids against degradation, for example photoinduced and/or thermooxidative degradation. Elastomers are given in the above list of possible organic materials.

Suitable lubricants and hydraulic fluids are based, for example, on mineral or synthetic oils or mixtures thereof. The lubricants are known to persons skilled in the an and are described in the relevant specialist literature, for example in Dieter Klamann, "Schmierstoffe und verwandte Produckte" [Lubricants and Related Products] (Verlag Chemie, Weinheim, 1982), in Schewe-Kobek, "Das Schmiermittel-Taschenbuch" [The Lubricant Handbook] (Dr. Alfred Hüthig-Verlag, Heidelberg, 1974), and in "Ullmanns Enzyklopädie der technischen Chemie" [Ullmann's Encyclopaedia of Industrial Chemistry], Vol. 13, pages 85–94 (Verlag Chemie, Weinheim, 1977).

The invention also relates to the stabilisation of organic materials against oxidative, thermal and/or actinic degradation by adding or applying, as stabilisers, compounds of the formula I to this material.

In addition to the compounds according to the invention, the compositions according to the invention, in particular if they contain organic, preferably synthetic polymers, may also contain further conventional additives. Examples of such additives are:

1. Antioxidants
   1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-di-cyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol and 2,6-di-nonyl-4-methylphenol.
   1.2. Alkylated hydroquinones, for example 2,6-di-tert-butyl-4-methoxyphenol, 2,5-di-tert-butylhydroquinone, 2,5-di-tert-amylhydroquinone and 2,6-diphenyl-4-octadecyloxyphenol.
   1.3. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol) and 4,4'-thiobis(6-tert-butyl-2-methylphenol).

1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene and bis[2-(3'-tert-butyl-2'-hydroxy-5'-methylbenzyl)-6-tert-butyl-4-methylphenyl]-terephthalate.

1.5. Benzyl compounds, for example, 1,3,5-tris(3,5-di-tert-butyl-4-hydroxybenzyl)-2,4,6-trimethylbenzene, bis(3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl)dithiol terephthalate, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, dioctadecyl 3,5-di-tert-butyl-4-hydroxybenzylphosphonate, the calcium salt of monoethyl 3,5-di-tert-butyl-4-hydroxybenzylphosphonate and 1,3,5-tris(3,5-dicyclohexyl-4-hydroxybenzyl)isocyanurate.

1.6. Acylaminophenols, for example 4-hydroxylauranilide, 4-hydroxystearanilide, 2,4-bis(octylmercapto)-6-(3,5-di-tert-butyl-4-hydroxyanilino)-s-triazine and octyl N-(3,5-di-tert-butyl-4-hydroxyphenyl)carbamate.

1.7. Esters of [β-(3,5-di-tert-butyl-4-hydroxyphenyl)-propionic acid with monohydric or polyhydric alcohols, for example with methanol, octadecanol, 1,6-hexanediol, neopentyl glycol, thiodiethylene glycol, diethylene glycol, triethylene glycol, pentaerythritol, tris(hydroxyethyl)isocyanurate and N,N'-bis(hydroxyethyl)oxalamide.

1.8. Esters of β-(5-tert-butyl-4-hydroxy-3-methylphenyl)propionic acid with monohydric or polyhydric alcohols, for example with methanol, octadecanol, 1,6-hexanediol, neopentyl glycol, thiodiethylene glycol, diethylene glycol, triethylene glycol, pentaerythritol, tris(hydroxy)ethyl isocyanurate and N,N'-bis(hydroxyethyl)oxalamide.

1.9. Esters of [β-(3,5-dicyclohexyl-4-hydroxyphenyl)propionic acid with monohydric or polyhydric alcohols, for example with methanol, octadecanol, 1,6-hexanediol, neopentyl glycol, thiodiethylene glycol, diethylene glycol, triethylene glycol, pentaerythritol, tris(hydroxy)ethyl isocyanurate and N,N'-bis(hydroxyethyl)oxalamide.

1.10. Amides of [β-(3,5-di-tert-butyl-4-hydroxyphenyl)propionic acid, for example N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine and N,N'-bis(3,5-di-tert-butyl-4-hydroxyphenylpropionyl)hydrazine.

2. UV Absorbers and Light Stabilisers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5-methyl, 3'-sec-butyl-5'-tert-butyl, 4'-octoxy, 3',5'-di-tert-amyl and 3',5'-bis(α,α-dimethylbenzyl) derivatives.

2.2. 2-Hydroxybenzophenones, for example the 4-hydroxy, 4-methoxy, 4-octoxy, 4-decyloxy, 4-dodecyloxy, 4-benzyloxy, 4,2',4'-hydroxy and 2'-hydroxy-4,4'-dimethoxy derivatives.

2.3. Esters of substituted or unsubstituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl or isooctyl α-cyano-β,β-diphenylacrylate, methyl α-carbomethoxycinnamate, methyl or butyl α-cyano-β-methyl-p-methoxycinnamate, methyl α-carbomethoxy-p-methoxycinnamate and N-(β-carbomethoxy-β-cyanovinyl)-2-methylindoline.

2.5 Nickel compounds, for example nickel complexes of 2,2'-thiobis[4-(1,1,3,3-tetramethylbutyl)phenol], such as the 1:1 complex or the 1:2 complex, if appropriate with additional ligands, such as n-butylamine, triethanolamine or N-cyclohexyldiethanolamine, nickel dibutyldithiocarbamate, nickel salts of monoalkyl 4-hydroxy-3,5-di-tert-butylbenzylphosphonates, such as the methyl or ethyl ester, nickel complexes of ketoximes, such as 2-hydroxy-4-methylphenyl undecyl ketoxime, and nickel complexes of 1-phenyl-4-lauroyl-5-hydroxypyrazole, if appropriate with additional ligands.

2.6. Sterically hindered amines, for example bis(2,2,6,6-tetramethylpiperidyl)sebacate, bis(1,2,2,6,6-pentamethylpiperidyl)sebacate, bis(1,2,2,6,6-pentamethylpiperidyl) n-butyl-3,5-di-tert-butyl-4-hydroxybenzylmalonate, the condensation product formed from 1-hydroxyethyl-2,2,6,6-tetramethyl-4-hydroxypiperidine and succinic acid, the condensation product formed from N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl) 1,2,3,4-butanetetraoate and 1,1'-(1,2-ethanediyl)bis(3,3,5,5-tetramethylpiperazinone).

2.7. Oxalic acid diamides, for example 4,4'-di-octyloxyoxanilide, 2,2'-di-octyloxy-5,5'-di-tert-butyloxanilide, 2,2'-di-dodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and a mixture thereof with 2-ethoxy-2'-ethyl-5,4'-di-tert-butyloxanilide or mixtures of o-methoxy- and p-methoxy-disubstituted oxanilides and of o-ethoxy- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine and 2-(2-hydroxy-4-dodecyloxyphenyl)-4,6-bis(2,4-dimethylphenyl)-1,3,5-triazine.

3. Metal deactivators, for example N,N'-diphenyloxalamide, N-salicylal-N'-salicyloylhydrazine, N,N'-bis(-salicyloyl)hydrazine, N,N'-bis(3,5-di-tert-butyl-4-hydroxyphenylpropionyl)hydrazine, 3-salicyloylamino-1,2,4-triazole and bis(benzylidene)oxalodihydrazide.

4. Further phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythrityl diphosphite, tris(2,4-di-tert-butylphenyl) phosphite, diisodecyl pentaerythrityl diphosphite, bis(2,4-di-tert-butylphenyl) pentaerythrityl diphosphite, tristearyl sorbitol triphosphite, tetrakis-(2,4-di-tert-butylphenyl) 4,4'-biphenylenediphosphonite and 3,9-bis(2,4-di-tert-butylphenoxy)-2,4,8,10-tetraoxa-3,9-diphosphaspiro[5.5]undecane.

5. Peroxide scavengers, for example esters of β-thiodipropionic acid, for example the lauryl, stearyl, myristyl and tridecyl esters, mercaptobenzimidazole, the zinc salt of 2-mercaptobenzimidazole, zinc dibutyldithiocarbamate, dioctadecyl disulfide and pentaerythrityl tetrakis(β-dodecylmercapto)propionate.

6. Benzofuranones and indolinones, as described, for example, in WO-A 80/01 566 and EP-A 4 15 887.

7. Polyamide stabilisers, for example copper salts in combination with iodides and/or phosphorus compounds and salts of divalent manganese.

8. Basic costabilisers, for example melamine, polyvinylpyrrolidone, dicyandiamide, triallyl cyanurate, urea derivatives, hydrazine derivatives, amines, polyamides, polyurethanes, alkali and alkaline earth metal salts of higher fatty acids, for example calcium stearate, zinc stearate, magnesium stearate, sodium ricinoleate and potassium palmitate, antimony pyrocatecholate and tin pyrocatecholate.

9. Nucleating agents, for example 4-tert-butylbenzoic acid, adipic acid and diphenylacetic acid.

10. Fillers and reinforcing agents, for example calcium carbonate, silicates, glass fibres, asbestos, talc, kaolin, mica, barium sulfate, metal oxides and hydroxides, carbon black and graphite.

11. Other additives, for example plasticisers, lubricants, emulsifiers, pigments, optical brighteners, flameproofing agents, antistatic and blowing agents.

The examples below illustrate the invention in greater detail. Pans and percentages, as in the claims and the remainder of the description, are by weight, unless stated otherwise.

EXAMPLE 1

Preparation of bis(2,4-di-tert-butyl-6-methylphenyl)phosphorochloridite 890.3 g (4 mol) of 2,4-di-tert-butyl-6-methylphenol, 4.2 g of dimethylformamide and 170.0 g of xylene are introduced into a four-neck flask which has been flushed with nitrogen and is fitted with a thermometer, dropping funnel, reflux condenser and distillation attachment. 274.9 g (2 mol) of phosphorus trichloride are added dropwise with stirring over the course of 1.5 hours at a temperature of 50° C. The reaction mixture is warmed to 130° C. and refluxed at this temperature for 1 hour. The reaction mixture is kept at 120° C. for 1 hour under a vacuum of 0.15 bar. Xylene is subsequently removed by distillation under a greater vacuum. After the vacuum has been broken using nitrogen, 959.5 g (1.9 mol) of the title compound are obtained as supercooled, yellow-orange, clear melt.

Purity: 98% (determined using $^{31}$P-NMR)

Purification: distillation at 204° C./0.0002 bar.

EXAMPLE 2

Preparation of bis(2,4-di-tert-butyl-6-methylphenyl)methyl phosphite 300 g (1.36 mol) of 2,4-di-tert-butyl-6-methylphenol are introduced into a 1500 ml sulfonation flask fitted with thermometer, stirrer and reflux condenser, and the reactor is flushed with nitrogen. The mixture is warmed to 55° C. in order to melt the phenol, and 1.5 g of dimethylformamide are added to the melt. 102.7 g (0.75 mol) of phosphorus trichloride are added dropwise over the course of 1.5 hours at the same temperature. The hydrochloric acid gas produced is neutralised by means of a 30% aqueous sodium hydroxide solution. When the addition is complete, the reaction mixture is heated to 140° C. over the course of 4 hours and stirred at this temperature for a further hour. A slight vacuum (0.55 bar) is then applied, and the mixture is stirred at 130° C. for a further 4 hours. The clear yellow-orange melt obtained (=bis(2,4-di-tert-butyl-6-methyl)phosphorochloridite) is then allowed to cool to about 80° C. in a nitrogen atmosphere and is diluted with 500 ml of petroleum ether (80°–100° C.). The solution is cooled to −5° C., and 89.3 g (0.884 mol) of triethylamine are added over the course of 15 minutes. 32.8 g (1.02 mol) of methanol are then added dropwise over the course of 1 hour, during which the temperature rises to +5° C. and the triethylamine hydrochloride precipitates. This mixture is allowed to warm slowly (about 1 hour) to room temperature with stirring. The precipitate is filtered off and the filtrate is evaporated, giving 328 g of phosphite as a yellow oil (purity determined by high pressure liquid chromatography [HPLC]: 94%). Recrystallisation of the crude product from ethanol gives 262 g (77% of theory) of the rifle compound in the form of a white powder having a melting point of 75°–78° C.

Elemental analysis: P calc.: 6.19% found: 6.19%

EXAMPLES 3–33

The compounds of Examples 3–33 are prepared analogously to the compound of Example 2 using the alcohol or phenol corresponding to the substituent $R^1$. The substituents and analytical data are shown in Table 1 below.

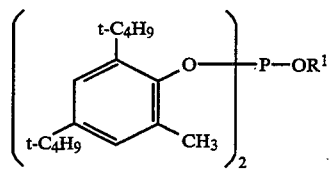

TABLE 1

| Example No. | $R_1$ | Yield [%] | Melting point [°C.] Refractive index $n_D^{20}$ | Elemental analysis % P calc. | % P found |
|---|---|---|---|---|---|
| 1 | $C_2H_5$ | 65 | 91 | 6.02 | 6.01 |
| 4 | $n\text{-}C_3H_7$ | 60 | 57–58 | 5.86 | 5.70 |
| 5 | $i\text{-}C_3H_7$ | 64 | 104–105 | 5.86 | 5.80 |
| 6 | $n\text{-}C_6H_{13}$ | 99 | high viscosity | 5.43 | 5.49 |
| 7 | $C_4H_9\text{—CH(C}_2H_5)\text{—CH}_2\text{—}$ | 95 | 1.5173 | 5.17 | 5.16 |
| 8 | $n\text{-}C_{12}H_{25}$ | 98 | 1.5107 | 4.73 | 4.71 |
| 9 | $i\text{-}C_{10}H_{21}$ | 95 | high viscosity | 4.94 | 4.99 |
| 10 | $i\text{-}C_{12/13}H_{25/27}$ | 79 | high viscosity | 4.67 | 4.65 |
| 11 | $n\text{-}C_{18}H_{37}$ | 93 | 1.5061 | 4.19 | 4.19 |
| 12 | $i\text{-}C_{18}H_{37}$ | 91 | 1.5036 | 4.19 | 4.10 |
| 13 | $-(CH_2)_2-OCH_3$ | 70 | yellowish oil | 5.69 | 5.44 |
| 14 | $-(CH_2CH_2-O)_3 C_4H_9$ | 97 | 1.5119 | 4.59 | 4.48 |
| 15 | $-(CH_2)_2-S-C_2H_5$ | 98 | high viscosity | 5.39 | 5.18 |
| 16 | $-(CH_2)_2-CF_3$ | 72 | 72 | 5.45 | 5.40 |
| 17 | $-(CH_2)_2-CN$ | 55 | 139 | 5.74 | 5.70 |
| 18 | $-(CH_2)_3-N(CH_3)_2$ | 65 | yellowish oil | 5.42 | 5.30 |
| 19 | $-CH_2CO_2-{}^nC_4H_9$ | 96 | high viscosity | 5.16 | 4.90 |
| 20 | benzyl | 97 | high viscosity | 5.37 | 5.46 |
| 21 | $-(CH_2)_2-C_6H_5$ | 74 | 78–80 | 5.24 | 5.18 |
| 22 | cyclohexyl | 64 | high viscosity | 5.45 | 5.22 |
| 23 | phenyl | 80 | 96–98 | 5.50 | 5.52 |
| 24 | naphthyl | 83 | 101–103 | 5.05 | 4.97 |
| 25 | $-C_6H_4-C_9H_{19}$ | 55 | 154–156 | 5.00 | 4.99 |
| 26 | $-C_6H_4-t\text{-}C_4H_9$ | 97 | high viscosity | 4.50 | 4.53 |
| 27 | $-C_6H_4-C(CH_3)_2-CH=CH_2$ | 99 | 1.5508 | 4.55 | 4.30 |
| 28 | $-C_6H_4-C(CH_3)_2-CH_2C(CH_3)_3$ | 78 | 117–120 | 4.59 | 4.44 |
| 29 | $-C(CH_3)_2-CH_2-C(CH_3)_2-N(CH_3)-CH_3$ (tetramethyl N-methyl piperidinyl) | 54 | 63–70 | 4.84 | 4.79 |
| 30 | tetramethylpiperidinyl NH | 32 | 55–75 | 4.95 | 4.81 |
| 31 | $-(CH_2)_2-N$(tetramethyl-4-hydroxypiperidinyl) | 87 | 69–78 | 4.62 | 4.60 |
| 32 | $-CH_2-CH=CH_2$ | 63 | 81–82 | 5.88 | 5.84 |

TABLE 1-continued

| Example No. | R₁ | Yield [%] | Melting point [°C] Refractive index $n_D^{20}$ | Elemental analysis % P calc. | % P found |
|---|---|---|---|---|---|
| 33 | 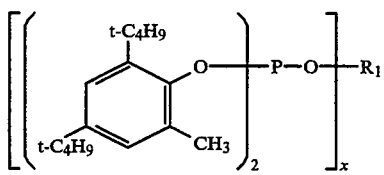 | 25 | high viscosity | 4.39 | 4.23 |

EXAMPLES 34–36

[structure shown: bis(2,4-di-tert-butyl-6-methyl)phenoxy-P-O-R₁ with subscript 2 and x]

The compounds of Examples 34–36 are prepared analogously to the compound of Example 2 using the polyol corresponding to the substituent R¹. Two equivalents of both bis(2,4-di-tert-butyl-6-methyl)phosphorochloridite and base are used for the compounds where x=2, and three equivalents of bis(2,4-di-tert-butyl-6-methyl) phosphorochloridite and three equivalents of base are correspondingly used for the trimeric compound (x=3). The substituents and analytical data are shown in Table 2 below.

TABLE 2

| Example No. | R₁ | x | Yield [%] | Melting point [°C] Refractive index $n_D^{20}$ | Elemental analysis % P calc. | % P found |
|---|---|---|---|---|---|---|
| 34 | —(CH₂)₆— | 2 | 49 | 168 | 5.87 | 5.82 |
| 35 | —(CH₂)₂—O—(CH₂)₂— | 2 | 75 | 40–50 (amorphous) | 5.94 | 5.36 |
| 36 | —(CH₂)₂—HN—(CH₂)₂— | 3 | 63 | 136–137 | 5.86 | 5.74 |

EXAMPLE 37

Stabilisation of Polypropylene 1.3 kg of polypropylene powder (melt flow index 3.2 g/10 min, measured at 230° C./2.16 kg) are mixed with 0.05% of calcium stearate, 0.05% of tetrakis[3,5-di-tert-butyl-4-hydroxyphenylpropionyloxymethyl]methane and 0.05% of the stabiliser indicated in Table 3. This mixture is extruded at 100 rpm in an extruder having a barrel diameter of 20 mm and a length of 400 mm, the 3 heating zones being set at 260° C., 270° C. and 280° C. The extrudate is cooled by drawing through a waterbath and is subsequently granulated. The granules obtained are extruded a second and third time. After these three extrusions, the melt flow index is measured at 230° C./2.16 kg. Small values indicate good stabilisation. The results are shown in Table 3.

TABLE 3

| Compound from Example No. | Melt flow index [g/10 min] |
|---|---|
| — | 17.8 |
| 2 | 6.1 |
| 3 | 6.6 |
| 4 | 5.8 |

TABLE 3-continued

| Compound from Example No. | Melt flow index [g/10 min] |
|---|---|
| 5 | 10.2 |
| 6 | 6.0 |
| 7 | 6.7 |
| 8 | 5.8 |
| 9 | 6.2 |
| 10 | 8.7 |
| 11 | 7.1 |
| 12 | 7.0 |
| 13 | 8.7 |
| 16 | 9.5 |

EXAMPLE 38

Stabilisation of Polyethylene 100 parts of unstabilised high-density polyethylene having a molecular weight of about 500,000 in powder form are mixed in the dry state with 0.05 part of tetrakis(3,5-di-tert-butyl-4-hydroxyphenylpropionyloxymethyl]methane and 0.1 part of the stabiliser indicated in Table 4. The mixture is kneaded for 50 minutes at 220° C. and 50 rpm in a Brabender Plastograph. During this time, the kneading resistance is recorded continuously as torque. As a consequence of the crosslinking of the polymer, a rapid increase in torque occurs during the kneading time after initially remaining constant. The effectiveness of the stabilisers is apparent from an increase in the time before the torque increases. The values obtained are shown in Table 4.

TABLE 4

| Compound from Example No. | Time before increase in torque [min] |
|---|---|
| — | 5.0 |
| 2 | 16.5 |
| 3 | 12.0 |
| 4 | 12.0 |
| 5 | 13.0 |
| 6 | 15.0 |
| 7 | 22.5 |
| 8 | 17.0 |
| 9 | 19.0 |
| 10 | 16.5 |
| 11 | 14.0 |
| 12 | 17.0 |
| 13 | 13.5 |

TABLE 4-continued

| Compound from Example No. | Time before increase in torque [min] |
|---|---|
| 16 | 15.0 |

What is claimed is:

1. A compound of the formula I

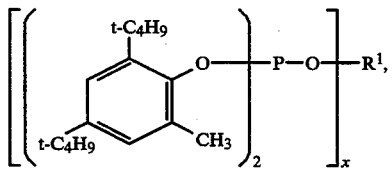

(I)

in which x is 1, 2 or 3, and, if $x=1$, $R^1$ is $C_1$-$C_{30}$alkyl, $C_1$-$C_{18}$alkyl substituted by halogen, —COOR$^2$, —CN, —NR$^3$R$^4$ or by —CONR$^3$R$^4$, $C_2$-$C_{18}$alkyl which is interrupted by —NR$^5$—, —O— or —S—, $C_3$-$C_{18}$alkenyl, $C_5$-$C_{12}$cycloalkyl, phenyl-$C_1$-$C_4$alkyl, phenyl or $R_1$ is naphthyl, a radical of the formula

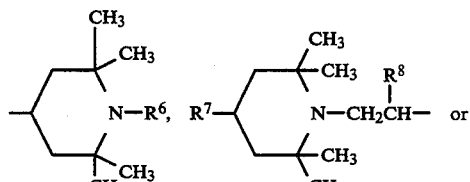

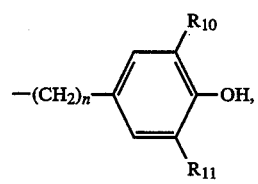

$R_2$, $R_3$, $R_4$ and $R_5$, independently of one another, are hydrogen, $C_1$-$C_{18}$alkyl, $C_5$-$C_{12}$cycloalkyl or phenyl-$C_1$-$C_4$alkyl, $R^6$ is hydrogen, methyl, allyl or benzyl, $R^7$ is hydrogen or —OR$^9$, $R^8$ is hydrogen or methyl, $R^9$ is hydrogen or $C_1$-$C_{30}$alkyl, $R^{10}$ and $R^{11}$, independently of one another, are hydrogen or $C_1$-$C_8$alkyl, and n is 3-6, with the proviso that $R^1$ is not a phenyl radical which is substituted in both ortho-positions to the carbon atom bonded to the oxygen atom, if $x=2$, $R^1$ is $C_2$-$C_{18}$alkylene, $C_2$-$C_{18}$alkylene which is interrupted by —NR$^5$—, —O— or —S—, or is a

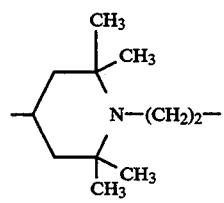

radical, and, if $x=3$, $R^1$ is $C_4$-$C_{12}$alkanetriyl or a

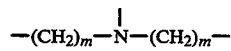

group in which m is 1-4.

2. A compound of the formula I according to claim 1, in which, if $x=1$, $R^1$ is $C_1$-$C_{30}$alkyl, $C_1$-$C_{18}$alkyl substituted by halogen, —COOR$^2$, —CN, —NR$^3$R$^4$ or by —CONR$^3$R$^4$, $C_2$-$C_{18}$alkyl which is interrupted by —NR$^5$—, —O— or —S—, $C_3$-$C_{18}$alkenyl, $C_5$-$C_{12}$cycloalkyl, phenyl-$C_1$-$C_4$alkyl, phenyl or $R_1$ is naphthyl, a radical of the formula

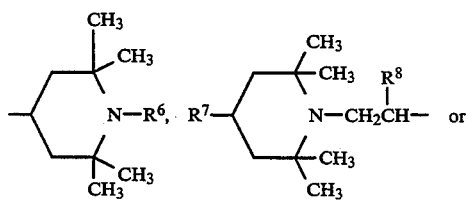

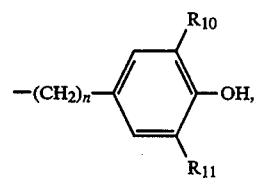

if $x=2$, $R^1$ is $C_2$-$C_{18}$alkylene, $C_2$-$C_{18}$alkylene which is interrupted by —NR$^5$—, —O— or —S—, or is a

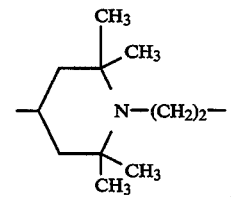

radical, and, if $x=3$, $R^1$ is $C_4$-$C_{12}$alkanetriyl or a

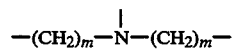

group in which m is 1-4.

3. A compound of the formula I according to claim 2, in which, if $x=1$, $R^1$ is $C_1$-$C_{24}$alkyl, $C_1$-$C_{12}$alkyl substituted by halogen, —COOR$^2$, —CN, —NR$^3$R$^4$ or by —CONR$^3$R$^4$, $C_2$-$C_{18}$alkyl which is interrupted by —NR$^5$—, —O— or —S—, $C_3$-$C_{18}$alkenyl, $C_5$-$C_{12}$cycloalkyl, phenyl-$C_1$-$C_4$alkyl, phenyl or $R_1$ is naphthyl, a radical of the formula

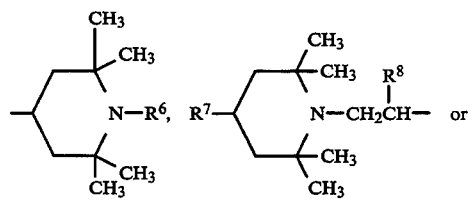

-continued

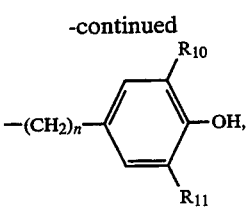

if x=2, R¹ is C₂-C₁₂alkylene, C₂-C₁₂alkylene which is interrupted by —NR⁵—, —O— or —S—, or is a

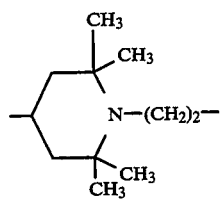

radical, and R¹⁰ and R¹¹, independently of one another, are hydrogen or C₁-C₄alkyl, and,
if x=3, R¹ is C₄-C₁₂alkanetriyl or a

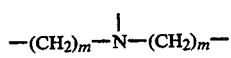

group in which m is 1-4.

4. A compound of the formula I according to claim 3, in which, if x=1, R¹ is C₁-C₂₀alkyl, C₁-C₈alkyl which is substituted by halogen, —COOR², —CN or —NR³R⁴, C₂-C₈alkyl which is interrupted by —O— or —S—, C₃-C₈alkenyl, C₅-C₈cycloalkyl, phenyl or R¹ is naphthyl, a radical of the formula

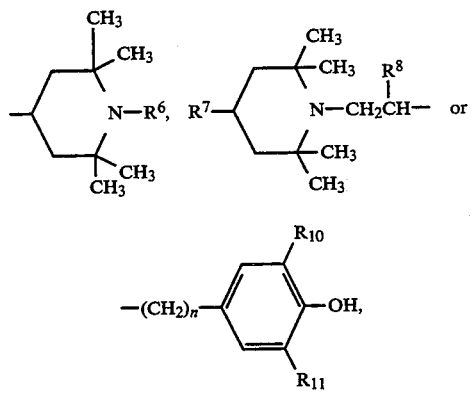

R⁶ is hydrogen or methyl, and R⁸ and R⁹ are hydrogen, if x=2, R¹ is C₂-C₈alkylene or C₂-C₈alkylene which is interrupted by —NR⁵— or —O—, and,
if x=3, R¹ is a

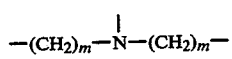

radical.

5. A compound of the formula I according to claim 3, in which, if x=1, R¹ is C₁-C₁₈alkyl which is unsubstituted or substituted by halogen, —COOR², —CN or —NR³R⁴, C₂-C₁₈alkyl which is interrupted by —NR⁵—, —O— or —S—, C₃-C₆alkenyl, C₅-C₈cycloalkyl, phenyl-C₁-C₄alkyl, a radical of the formula

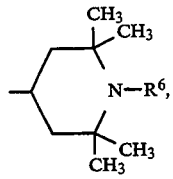

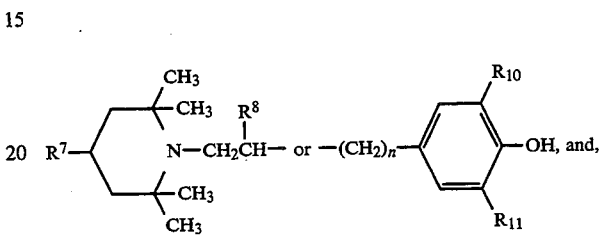

if x=2, R¹ is C₂-C₁₂alkylene, C₂-C₁₂alkylene which is interrupted by —NR⁵—, —O— or —S—, or is a

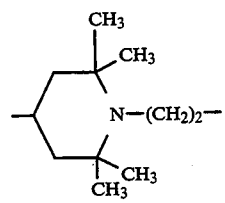

radical, and,
if x=3, R¹ is C₄-C₁₂alkanetriyl or a

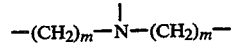

group.

6. A compound according to claim 5, in which x=1, R¹ is C₁-C₁₂alkyl which is unsubstituted or substituted by halogen, —COOR², —CN or —NR³R⁴, C₂-C₁₂alkyl which is interrupted by —NR⁵—, —O— or —S—, or is phenyl-C₁-C₄alkyl or C₅-C₇cycloalkyl.

7. A compound according to claim 1, in which R¹ is C₁-C₁₈alkyl, C₅-C₇cycloalkyl or phenyl-C₁-C₄alkyl.

8. A compound according to claim 7, in which R¹ is C₁-C₄alkyl.

9. The compound of the formula II

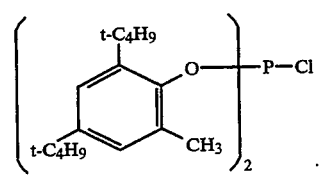

(II)

* * * * *